United States Patent [19]
Satoh et al.

[11] Patent Number: 5,101,057
[45] Date of Patent: Mar. 31, 1992

[54] FLUORINATED CARBOXYLIC ACID DERIVATIVES AND METHODS FOR MAKING

[75] Inventors: Shinichi Satoh, Annaka; Noriyuki Koike, Gunma; Hideki Fujii, Annaka, all of Japan

[73] Assignee: Shin-Etsu Chemical Co., Ltd., Tokyo, Japan

[21] Appl. No.: 562,320

[22] Filed: Aug. 3, 1990

[30] Foreign Application Priority Data

Aug. 3, 1989 [JP] Japan .................. 1-202115

[51] Int. Cl.⁵ ............................ C07F 7/08; C07F 7/18
[52] U.S. Cl. ............................ 556/437; 556/442
[58] Field of Search ........................ 556/437, 442

[56] References Cited

U.S. PATENT DOCUMENTS

| | | | |
|---|---|---|---|
| 3,012,006 | 12/1961 | Holbrook et al. ........... | 556/437 X |
| 3,560,542 | 2/1971 | Kim et al. ................... | 556/437 |
| 3,639,156 | 2/1972 | Pittman et al. .............. | 556/437 X |
| 3,681,418 | 8/1972 | Pierce et al. ................ | 556/437 |

FOREIGN PATENT DOCUMENTS 3017926 11/1980 Fed. Rep. of Germany ...... 556/437
54-11953 1/1979 Japan .

*Primary Examiner*—Paul F. Shaver
*Attorney, Agent, or Firm*—Birch, Stewart, Kolasch & Birch

[57] ABSTRACT

Novel fluorinated carboxylic acid derivatives of the general formula:

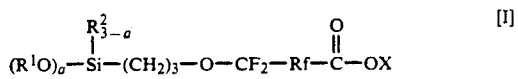

wherein $R^1$ and $R^2$ are independently selected from substituted or unsubstituted monovalent hydrocarbon groups, Rf is a divalent perfluoroalkyl or perfluoropolyether group, X is a hydrogen atom or triorganosilyl group, and a is equal to 2 or 3 are useful curing catalysts for RTV organopolysiloxane compositions. These fluorinated carboxylic acid derivatives are prepared by effecting hydrosilylation between alkenyl-containing fluorinated carboxylic acid derivatives and hydrosilanes in the presence of catalysts.

6 Claims, 6 Drawing Sheets

FLUORINATED CARBOXYLIC ACID DERIVATIVES AND METHODS FOR MAKING

The present invention relates to novel fluorinated carboxylic acid derivatives useful as curing catalysts for room temperature vulcanizable organopolysiloxane compositions and a method for preparing the same.

BACKGROUND OF THE INVENTION

Organopolysiloxane compositions, which remain stable and free flowing during shelf storage in a sealed condition, but when exposed to ambient air, cure into rubbery elastomers at room temperature under the action of humidity are known in the art as room temperature vulcanizable (RTV) organopolysiloxane compositions. They have been widely used as sealants, coatings, and adhesives in building, machinery, electrical and other industrial fields.

RTV organopolysiloxane compositions are generally classified into the acetate type, oxime type, alcohol type, hydroxyamine type, and amine type depending on the type of compound to be eliminated. The compositions of the acetate, oxime, hydroxyamine, and amine types are undesirably corrosive to the surrounding metal while the compositions of the alcohol type, become unlikely to cure after long-term storage.

To overcome these drawbacks, Japanese Patent Application Kokai No. 11953/1979 proposes an RTV organopolysiloxane composition which is shelf stable and does not corrode the surrounding metal. This composition, however, tends to yellow under the influence of ultraviolet rays and heat and does not cure under acidic conditions since the curing catalyst is a guanidine compound.

There is a need for a curing catalyst which can be added to RTV organopolysiloxane compositions, to render them non-corrosive to metals, shelf stable, discoloration resistant, and curable under acidic conditions.

SUMMARY OF THE INVENTION

The present inventors have found that by reacting a compound, terminated with an acid fluoride at each end and having the general formula:

wherein Rf is a divalent perfluoroalkyl or perfluoropolyether group of the general formula:

wherein n is an integer of from 0 to 8, m and l are integers of from 0 to 3, j and k are equal to 0 or 1, with the proviso that j=k=l=m=0 when n=0, m=0 when j=0, and l=0 when k=0, with an alkali fluoride and then with an allyl halide, there can be produced a novel fluorinated carboxylic acid fluoride of the general formula:

wherein Rf is as defined above. The acid fluoride of formula [IV] is then hydrolyzed into a carboxylic acid, which is then in turn reacted with a triorganosilylating agent to form an alkenyl-containing fluorinated carboxylic acid derivative of general formula [III]:

wherein Rf is as defined above and X is a hydrogen atom or triorganosilyl group. Then, by effecting hydrosilylation between the alkenyl-containing fluorinated carboxylic acid derivative of general formula [III] and a hydrosilane of general formula [II]:

wherein $R^1$ and $R^2$ are independently selected from substituted or unsubstituted monovalent hydrocarbon groups, and letter a is equal to 2 or 3 in the presence of an organic platinum complex catalyst, there can be synthesized a novel fluorinated carboxylic acid derivative of general formula [I]:

wherein $R^1$, $R^2$, Rf, X and a are as defined above. This compound is an effective curing catalyst for RTV organopolysiloxane compositions of the condensation type, providing RTV organopolysiloxane compositions which are noncorrosive to metals, shelf stable, discoloration resistant, and well curable under acidic conditions.

The present invention is predicated on these findings.

DETAILED DESCRIPTION OF THE INVENTION

The novel fluorinated carboxylic acid derivatives of the present invention are of general formula [I].

In formula [I], $R^1$ and $R^2$, which may be the same or different, are independently selected from substituted or unsubstituted monovalent hydrocarbon groups. The substituted or unsubstituted monovalent hydrocarbon groups represented by $R^1$ include alkyl groups such as methyl, ethyl, and propyl; alkenyl groups such as vinyl and allyl; cycloalkyl groups such as cyclopentyl and cyclohexyl; aryl groups such as phenyl and tolyl; alkenyloxy groups such as isopropenoxy and isobutenoxy; and haloalkyl groups such as 2,2,2-trifluoroethoxy and 3,3,3-trifluoro-2-trifluoropropoxy. The substituted or unsubstituted monovalent hydrocarbon groups represented by $R^2$ include alkyl groups such as methyl, ethyl, and propyl; alkenyl groups such as vinyl and allyl; cycloalkyl groups such as cyclopentyl and cyclohexyl; aryl groups such as phenyl and tolyl; and haloalkyl groups such as 3,3,3-trifluoropropyl and 3,3,4,4,5,5,6,6-nonafluorohexyl.

In formula [I], Rf is a divalent perfluoroalkyl or perfluoropolyether group of the general formula:

wherein n is an integer of from 0 to 8, m and l are integers of from 0 to 3, j and k are each equal to 0 or 1, with the proviso that $j=k=l=m=0$ when $n=0$, $m=0$ when $j=0$, and $l=0$ when $k=0$; X is a hydrogen atom or triorganosilyl group; and letter a is equal to 2 or 3.

The triorganosilyl groups represented by X include trimethylsilyl, vinyldimethylsilyl, triethylsilyl, trivinylsilyl, phenyldimethylsilyl, 3,3,3-trifluoropropyldimethylsilyl, and 3,3,4,4,5,5,6,6-nonafluorohexyldimethylsilyl groups.

Several illustrative, non-limiting examples of the compound of formula [I] are shown below. In the following formulae, Vi is vinyl and Ph is phenyl.

$(CH_3O)_3Si(CH_2)_3OCF_2COOH$

$(F_3CCH_2O)_3Si(CH_2)_3OCF_2COOSi(CH_3)_3$

$(CH_3O)_3Si(CH_2)_3O(CF_2)_4COOH$

$(CH_3O)_3Si(CH_2)_3O(CF_2)_5COOSi(CH_3)_3$

$(CF_3CH_2O)_3Si(CH_2)_3O(CF_2)_5COOSi(CH_3)_3$

The novel fluorinated carboxylic acid derivatives of formula [I] are prepared by the following sequence of reactions, for example.

First, an alkenyl-containing fluorinated acid fluoride of general formula [IV]:

wherein Rf is as defined above is prepared by reacting (a) a compound terminated with acid fluoride at each end having the general formula:

wherein Rf is as defined above, with (b) an alkali fluoride such as cesium fluoride in a polar solvent, and adding dropwise (c) an allyl halide to the reaction mixture.

In this reaction, the molar ratio (b/a) of alkali fluoride (b) to acid fluoride-terminated compound (a) is preferably 1 or higher, more preferably from 1.2 to 1.7, and the molar ratio (c/a) of allyl fluoride (c) to acid fluoride-terminated compound (a) is preferably 1 or higher, more preferably from 1.5 to 2. The reaction temperature preferably ranges from 50° to 100° C. The allyl halides used herein include allyl chloride, allyl bromide and allyl iodide. The polar solvents used herein include ether solvents such as diglyme (diethylene glycol dimethyl ether) and tetraglyme.

Next, by hydrolyzing the acid fluoride of formula [IV], there is produced the corresponding carboxylic acid. If desired, the carboxylic acid is reacted with a triorganosilylating agent to form an alkenyl-containing fluorinated carboxylic acid derivative of general formula [III]:

wherein Rf and X are as defined above. Finally, by effecting hydrosilylation between the fluorinated carboxylic acid or derivative of formula [III] and a hydrosilane of general formula [II]:

wherein $R^1$, $R^2$, and a are as defined above in the presence of an organic platinum complex catalyst, there can be synthesized a fluorinated carboxylic acid derivative of general formula [I]:

wherein $R^1$, $R^2$, Rf, X and a are as defined above.

It will be understood that a carboxylic acid of formula [I] wherein X is hydrogen can also be produced by hydrolyzing a compound of formula [I] wherein X is a triorganosilyl group.

In the hydrosilylation reaction, the molar ratio (II/III) of hydrosilane of formula [II] to alkenyl-containing fluorinated carboxylic acid derivative of formula [III] is preferably 1 or higher, more preferably from 1 to 1.5. The organic platinum complex is present in a concentration of $1 \times 10^{-3}$ to $1 \times 10^{-6}\%$. The reaction may be carried out in a solvent which is usually benzene, toluene, xylene or hexane.

The fluorinated carboxylic acid derivatives of formula [I] are useful curing catalysts for room temperature vulcanizable organopolysiloxane compositions of the condensation type which can be utilized as sealants, coatings, adhesives, and insulators in various industrial fields as will be evident from Reference Examples shown later.

EXAMPLE

Examples of the present invention are given below by way of illustration and not by way of limitation. Unless otherwise stated, parts and percents are by weight.

EXAMPLE 1

A 2-liter, four-necked flask equipped with a reflux condenser and a stirrer was charged with 434 grams of cesium fluoride and 880 grams of tetraglyme. With stirring, 600 grams of perfluoroadipic fluoride was added in increments through a dropping funnel. Then 321 grams of allyl bromide was added dropwise over 30 minutes through the dropping funnel. Using an oil bath, the flask was heated to keep the contents at 70° C. and stirring was continued for 24 hours at the temperature. At the end of reaction, the flask was cooled down to room temperature. After the precipitate was filtered off, the filtrate was distilled, yielding 350 grams of a fraction having a boiling point of 88°–90° C./140 mmHg. On analysis, this product was identified to be a compound of formula [IVa] shown below. The yield was 48%.

$$CH_2=CH-CH_2O(CF_2)_5COF \qquad [IVa]$$

| Analysis | | | | |
|---|---|---|---|---|
| ¹H-NMR: δ (ppm) | | | | |
| $CH_2=$ | 5.49 | | | |
| $=CH-$ | 6.10 | | | |
| $-CH_2O-$ | 4.70 | | | |
| GC-MS: | | | | |
| $(M + H)^+$ | 355 | | | |
| IR: | | | | |
| $>C=O$ | 1880 cm$^{-1}$ | | | |
| Elemental analysis: | | | | |
| | C | H | O | F |
| Calcd. (%) | 30.5 | 1.4 | 9.0 | 59.0 |
| Found (%) | 30.6 | 1.3 | 9.2 | 58.6 |

Next, a 500-ml, four-necked flask equipped with a reflux condenser and a stirrer was charged with 62 grams of water and 36 grams of sodium fluoride. Using an ice water bath, the flask was cooled until the contents reached 10° C. With stirring, 300 grams of the compound of formula [IVa] prepared above was added dropwise through a dropping funnel. The rate of addition was controlled such that the contents did not exceed 20° C. After the completion of addition, the ice water bath was removed and stirring was continued for 3 hours. The solids were removed from the flask contents by filtration, and the filtrate was then distilled, yielding 265 grams of a fraction having a boiling point of 93°–99° C./2 mmHg. On analysis, this product was identified to be a compound of formula [IIIa] shown below. The yield was 88%.

$$CH_2=CH-CH_2O(CF_2)_5COOH \qquad [IIIa]$$

| Analysis | | | | |
|---|---|---|---|---|
| ¹H-NMR: δ (ppm) | | | | |
| $CH_2=$ | 5.45 | | | |
| $=CH-$ | 6.08 | | | |
| $-CH_2-O-$ | 4.63 | | | |
| $-COOH$ | 11.4 | | | |
| GC-MS: | | | | |
| $(M + H)^+$ | 353 | | | |
| IR: | | | | |
| $>C=O$ | 1780 cm$^{-1}$ | | | |
| Elemental analysis: | | | | |
| | C | H | O | F |
| Calcd. (%) | 30.7 | 1.7 | 13.6 | 54.0 |
| Found (%) | 30.8 | 1.6 | 13.3 | 54.1 |

Next, a 500-ml, four-necked flask equipped with a reflux condenser and a stirrer was charged with 48 grams of bistrimethylsilylacetamide and 100 grams of toluene. With stirring, 150 grams of the compound of formula [IIIa] prepared above was added dropwise through a dropping funnel. The rate of addition was controlled such that the contents did not exceed 50° C. After the completion of addition, stirring was continued for 2 hours at room temperature. The flask contents were then distilled, yielding 156 grams of a fraction having a boiling point of 93.0°–93.5° C./6 mmHg. On analysis, this product was identified to be a compound of formula [IIIb] shown below. The yield was 86%.

$$CH_2=CHCH_2O(CF_2)_5COOSi(CH_3)_3 \qquad [IIIb]$$

| Analysis | | | | | |
|---|---|---|---|---|---|
| ¹H-NMR: δ (ppm) | | | | | |
| $CH_2=$ | 5.39 | | | | |
| $=CH-$ | 6.03 | | | | |
| $-CH_2-O-$ | 4.66 | | | | |
| $-Si(CH_3)_3$ | 0.50 | | | | |
| GC-MS: | | | | | |
| $(M + H)^+$ | 425 | | | | |
| IR: | | | | | |
| $>C=O$ | 1770 cm$^{-1}$ | | | | |
| Elemental analysis: | | | | | |
| | C | H | O | F | Si |
| Calcd.(%) | 34.0 | 3.3 | 11.3 | 44.8 | 6.6 |
| Found (%) | 34.2 | 3.2 | 11.3 | 44.7 | 6.5 |

Next, a 200-ml, three-necked flask equipped with a reflux condenser, magnetic stirrer, and thermometer was charged with 70.0 grams of the compound of formula [IIIb] prepared above. Using an oil bath, the flask was heated to keep the contents at 70° C. After 0.01 gram of a 10% toluene solution of chloroplatinic acid was added, 24.2 grams of trimethoxysilane was slowly added through a dropping funnel. The rate of addition was controlled such that the contents were at 70° to 100° C. After the completion of addition, stirring was continued for one hour at 70° C. At the end of reaction, the flask contents were poured into a distillation flask. The flask was heated by an oil bath adjusted at 80° C. while the flask interior was evacuated up to 2 mmHg by means of a vacuum pump. The volatile contents were distilled off in this way, leaving 85.2 grams of a nonvolatile liquid in the flask. On analysis, this product was identified to be a compound of formula [Ia] shown below. The yield was 95%.

$(CH_3O)_3SiCH_2CH_2CH_2O(CF_2)_5COOSi(CH_3)_3$      [Ia]

Analysis $^1$H-NMR:

$\overset{1}{(CH_3O)_3}Si\overset{2}{CH_2}\overset{3}{CH_2}\overset{4}{CH_2}O(CF_2)_5COO\overset{5}{Si(CH_3)_3}$

| | δ (ppm) |
|---|---|
| 1 | 3.51 |
| 2 | 1.01 |
| 3 | 1.91 |
| 4 | 4.17 |
| 5 | 0.51 |

GC-MS:
(M + H)$^+$      546

IR:
$>C=O$      1770 cm$^{-1}$

Figure 1:
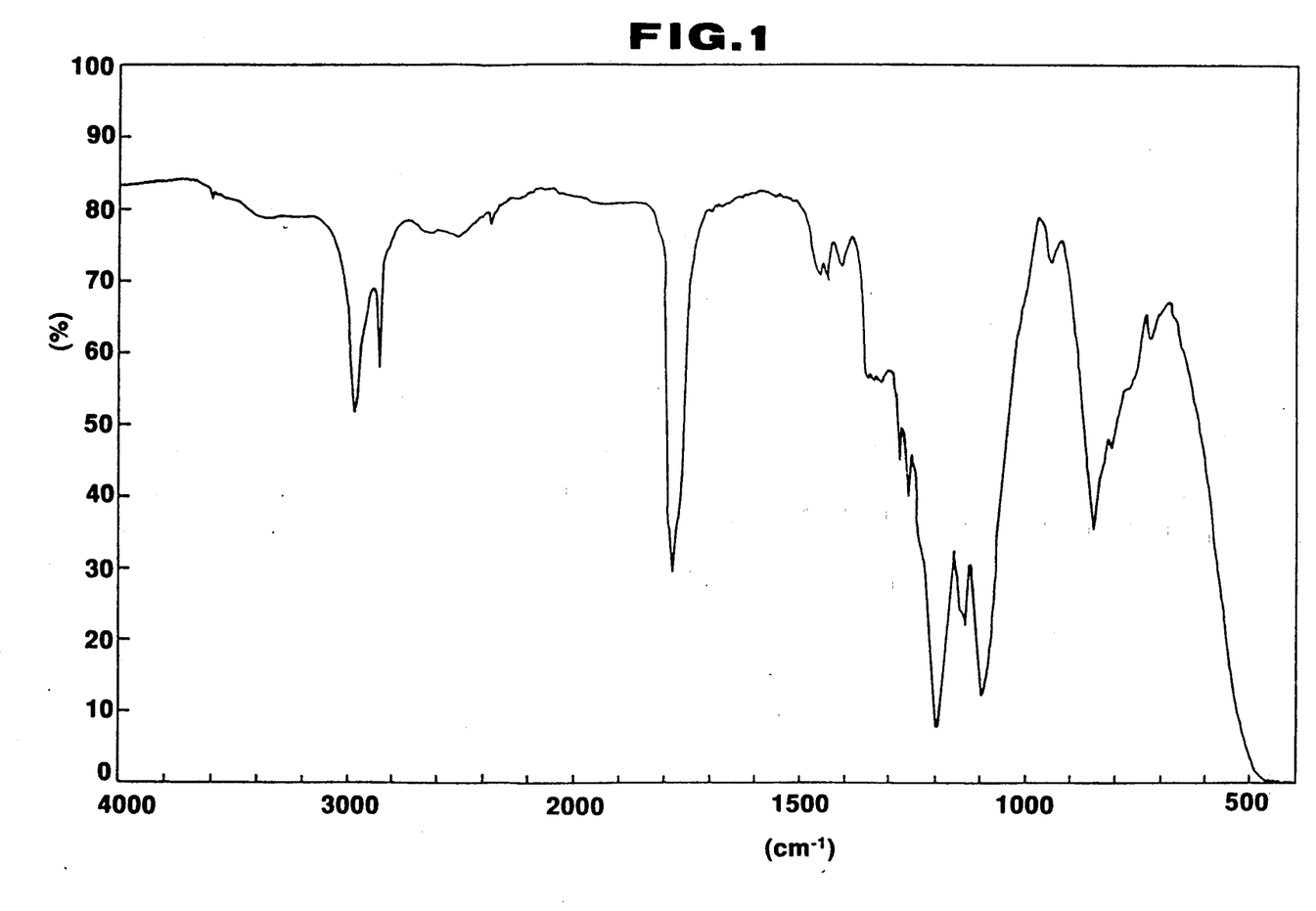
FIGS. 1 to 6 are diagrams showing IR spectra of the end compounds of Examples 1 to 6, respectively.

IR spectrum is shown in the chart of FIG. 1.

EXAMPLE 2

A 200-ml, three-necked flask equipped with a reflux condenser, magnetic stirrer, and thermometer was charged with 70 grams of the compound of formula [IIIb] obtained in Example 1. Using an oil bath, the flask was heated to keep the contents at 70° C. After 0.01 gram of a 10% toluene solution of chloroplatinic acid was added, 31.3 grams of diisopropenoxymethylsilane was slowly added through a dropping funnel. The rate of addition was controlled such that the contents were at 70° to 100° C. After the completion of addition, stirring was continued for one hour at 70° C. At the end of reaction, the flask contents were poured into a distillation flask. The flask was heated by an oil bath adjusted at 80° C. while the flask interior was evacuated up to 2 mmHg by means of a vacuum pump. The volatile contents were distilled off in this way, leaving 89.5 grams of a non-volatile liquid in the flask. On analysis, this product was identified to be a compound of formula [Ib] shown below. The yield was 93%.

$$(CH_2=\overset{CH_3}{\underset{CH_3}{\overset{|}{C}}}-O)_2-Si-CH_2CH_2CH_2O(CF_2)_5COOSi(CH_3)_3 \quad [Ib]$$

Analysis $^1$H-NMR:

$$(\overset{\overset{1}{CH_2}\diagdown}{\underset{\underset{2}{CH_3}\diagup}{}}\overset{3}{C}-O)_2-\overset{}{\underset{}{Si}}-\overset{4}{CH_2}\overset{5}{CH_2}\overset{6}{CH_2}O(CF_2)_5COO\overset{7}{Si(CH_3)_3}$$

| | δ (ppm) |
|---|---|
| 1 | 4.21 |
| 2 | 1.97 |
| 3 | 0.34 |
| 4 | 1.02 |
| 5 | 1.92 |
| 6 | 4.18 |
| 7 | 0.51 |

GC-MS:
(M + H)$^+$      583

IR:
$>C=O$      1770 cm$^{-1}$

Figure 2:
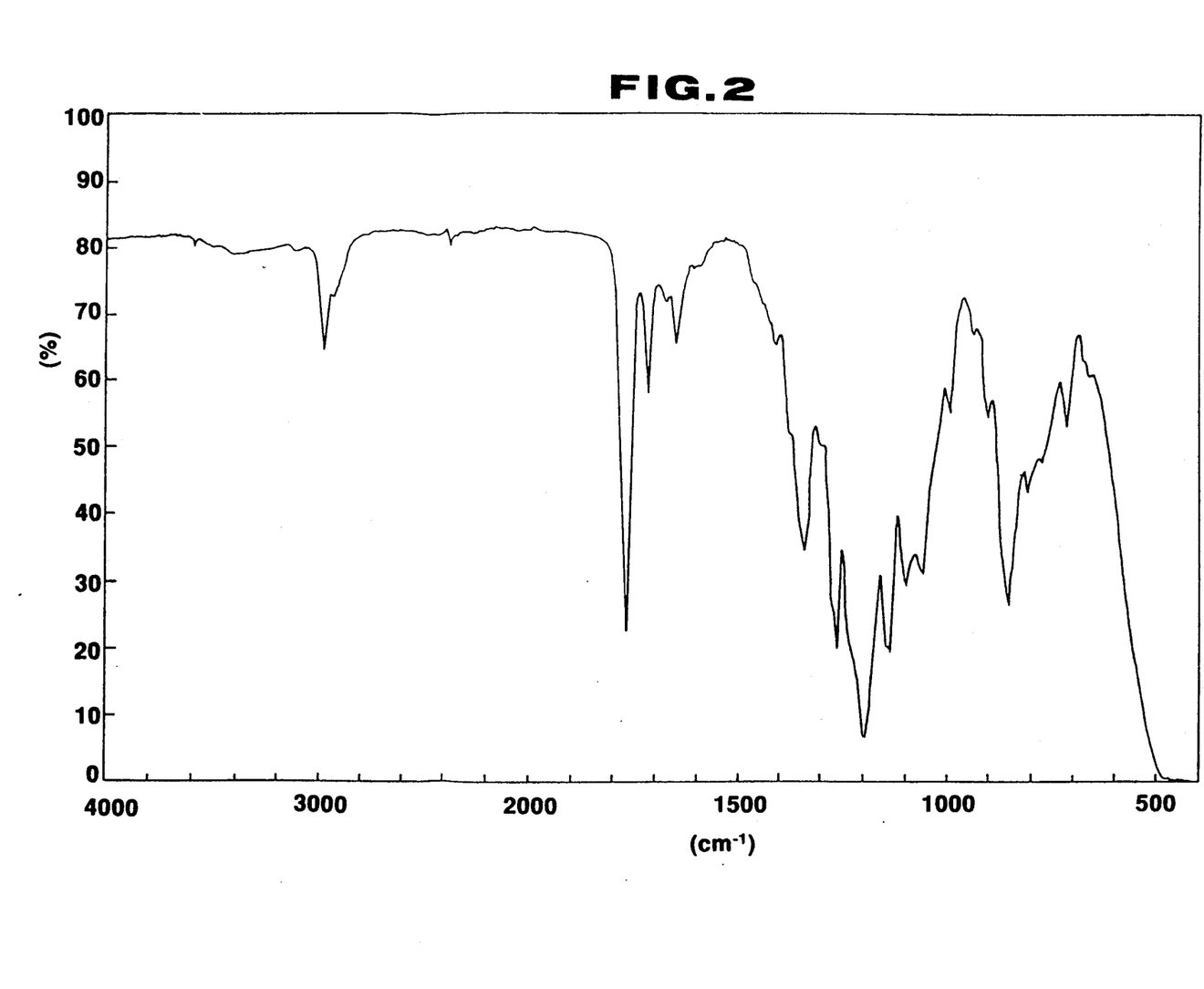

IR spectrum is shown in the chart of FIG. 2.

Elemental analysis:

| | C | H | O | F | Si |
|---|---|---|---|---|---|
| Calcd. (%) | 39.2 | 4.8 | 13.7 | 32.6 | 9.6 |
| Found (%) | 39.1 | 4.9 | 13.7 | 32.4 | 9.7 |

EXAMPLE 3

A 200-ml, three-necked flask equipped with a reflux condenser, magnetic stirrer, and thermometer was charged with 70 grams of the compound of formula [IIIb] obtained in Example 1. Using an oil bath, the flask was heated to keep the contents at 70° C. After 0.01 gram of a 10% toluene solution of chloroplatinic acid was added, 64.5 grams of tris(2,2,2-trifluoroethoxy)silane was slowly added through a dropping funnel. The rate of addition was controlled such that the contents were at 70° to 100° C. After the completion of addition, stirring was continued for one hour at 70° C. At the end of reaction, the flask contents were poured into a distillation flask. The flask was heated by an oil bath adjusted at 80° C. while the flask interior was evacuated up to 2 mmHg by means of a vacuum pump. The volatile contents were distilled off in this way, leaving 120.3 grams of a non-volatile liquid in the flask. On analysis, this product was identified to be a compound of formula [Ic] shown below. The yield was 97%.

$(CF_3CH_2O)_3SiCH_2CH_2CH_2O(CF_2)_5COOSi(CH_3)_3$      [Ic]

Analysis $^1$H-NMR:

$(CF_3\overset{1}{CH_2}O)_3Si\overset{2}{CH_2}\overset{3}{CH_2}\overset{4}{CH_2}O(CF_2)_5COO\overset{5}{Si(CH_3)_3}$

| | δ (ppm) |
|---|---|
| 1 | 4.17 |
| 2 | 4.17 |
| 3 | 1.91 |
| 4 | 1.01 |
| 5 | 0.51 |

GC-MS:
(M + H)$^+$      751

IR:
$>C=O$      1770 cm$^{-1}$

Figure 3:
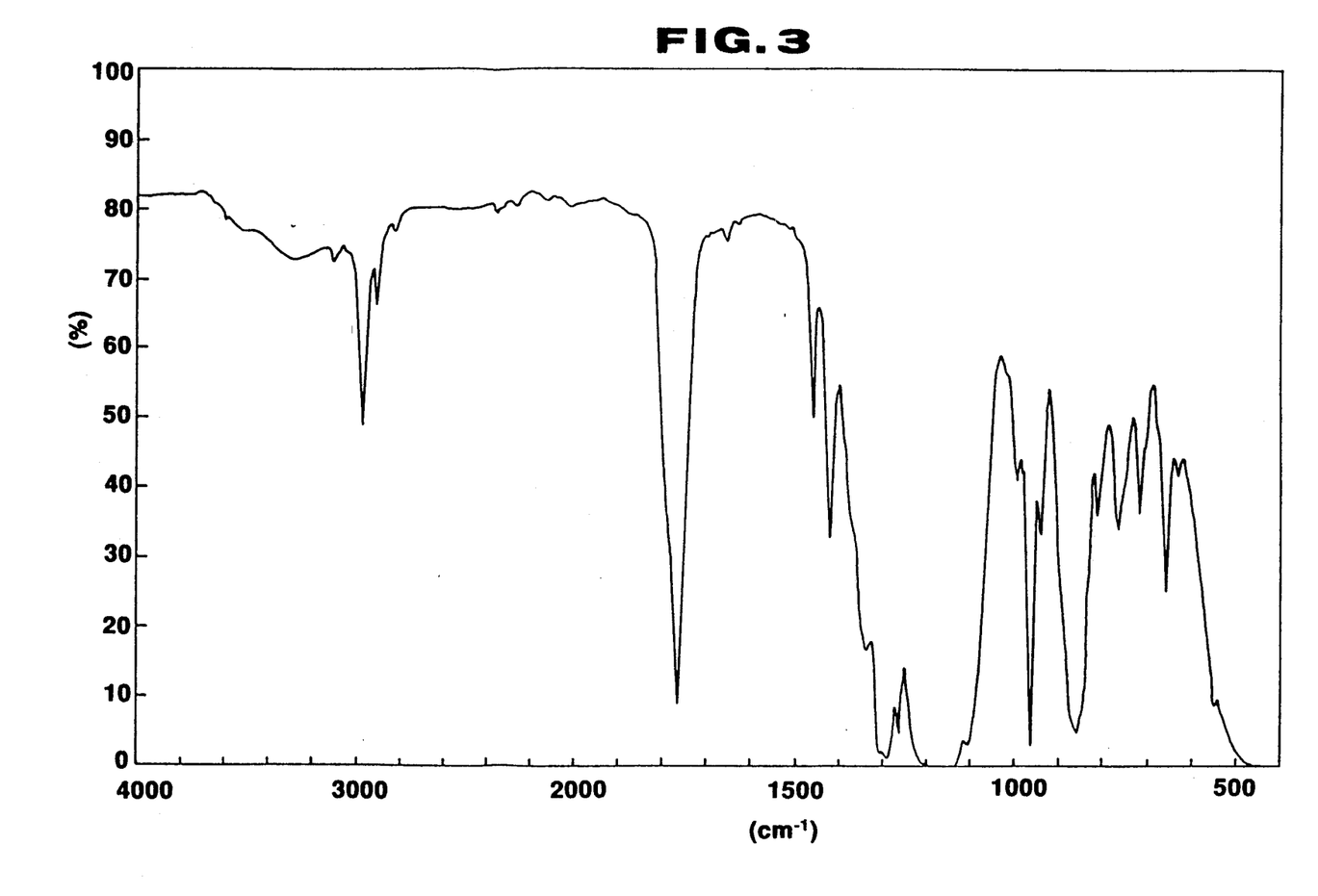

IR spectrum is shown in the chart of FIG. 3.

Elemental analysis:

| | C | H | O | F | Si |
|---|---|---|---|---|---|
| Calcd. (%) | 28.8 | 2.8 | 12.8 | 48.1 | 7.5 |
| Found (%) | 29.0 | 2.6 | 12.9 | 48.3 | 7.2 |

EXAMPLE 4

A 2-liter, four-necked flask equipped with a reflux condenser and a stirrer was charged with 500 grams of cesium fluoride and 1000 grams of tetraglyme. With stirring. 1000 grams of an acid fluoride-terminated compound of the formula:

$$\text{FOCCFOCF}_2\text{CF}_2\text{OCFCOF}$$
$$\quad\ \ |\qquad\qquad\quad\ |$$
$$\quad\ \ \text{CF}_3\qquad\quad\ \ \text{CF}_3$$

was added in increments through a dropping funnel. Then 371 grams of allyl bromide was added dropwise over 30 minutes through the dropping funnel. Using an oil bath, the flask was heated to keep the contents at 70° C. and stirring was continued for 24 hours at the temperature. At the end of reaction, the flask was cooled to room temperature. After the precipitate was filtered off, the filtrate was distilled, yielding 503 grams of a fraction having a boiling point of 104°–106° C./140 mmHg. On analysis, this product was identified to be a compound of formula [IVb] shown below.

$$\text{CH}_2=\text{CH}-\text{CH}_2\text{OCF}_2\text{CFOCF}_2\text{CF}_2\text{OCFCOF} \quad [\text{IVb}]$$
$$\qquad\qquad\qquad\qquad\quad\ |\qquad\qquad\qquad\ |$$
$$\qquad\qquad\qquad\qquad\ \ \text{CF}_3\qquad\qquad\ \ \text{CF}_3$$

Analysis

| $^1$H-NMR: δ (ppm) | |
|---|---|
| CH$_2$= | 5.47 |
| =CH— | 6.08 |
| —CH$_2$—O— | 4.69 |
| GC-MS: | |
| (M + H)$^+$ | 487 |
| IR: | |
| >C=O | 1880 cm$^{-1}$ |

Elemental analysis:

| | C | H | O | F |
|---|---|---|---|---|
| Calcd. (%) | 27.2 | 1.0 | 13.2 | 58.5 |
| Found (%) | 27.1 | 1.1 | 13.0 | 58.3 |

Next, a 500-ml, four-necked flask equipped with a reflux condenser and a stirrer was charged with 45 grams of water and 26 grams of sodium fluoride. Using an ice water bath, the flask was cooled until the contents reached 10° C. With stirring, 300 grams of the compound of formula [IVb] prepared above was added dropwise through a dropping funnel. The rate of addition was controlled such that the contents did not exceed 20° C. After the completion of addition, the ice water bath was removed and stirring was continued for 3 hours at room temperature. The solids were removed from the flask contents by filtration, and the filtrate was then distilled, yielding 268 grams of a fraction having a boiling point of 108°–110° C./3 mmHg. On analysis, this product was identified to be a compound of formula [IIIc] shown below. The yield was 90%.

$$\text{CH}_2=\text{CH}-\text{CH}_2\text{OCF}_2\text{CFOCF}_2\text{CF}_2\text{OCFCOOH} \quad [\text{IIIc}]$$
$$\qquad\qquad\qquad\qquad\quad\ |\qquad\qquad\qquad\ \ |$$
$$\qquad\qquad\qquad\qquad\ \ \text{CF}_3\qquad\qquad\ \ \text{CF}_3$$

Analysis

| $^1$H-NMR: δ (ppm) | |
|---|---|
| CH$_2$= | 5.43 |
| =CH— | 6.04 |
| —CH$_2$—O— | 4.66 |
| —COOH | 11.5 |
| GC-MS: | |
| (M – H)$^+$ | 485 |
| IR: | |
| >C=O | 1780 cm$^{-1}$ |

Elemental analysis:

| | C | H | O | F |
|---|---|---|---|---|
| Calcd. (%) | 27.3 | 1.2 | 16.5 | 54.9 |
| Found (%) | 27.1 | 1.3 | 16.8 | 54.5 |

Next, a 500-ml, four-necked flask equipped with a reflux condenser and a stirrer was charged with 47 grams of bistrimethylsilylacetamide and 134 grams of toluene. With stirring, 200 grams of the compound of formula [IIIc] prepared above was added dropwise through a dropping funnel. The rate of addition was controlled such that the contents did not exceed 50° C. After the completion of addition, stirring was continued for 2 hours at room temperature. The flask contents were then distilled, yielding 197 grams of a fraction having a boiling point of 97°–99° C./6 mmHg. On analysis, this product was identified to be a compound of formula [IIId] shown below. The yield was 85%.

$$\text{CH}_2=\text{CH}-\text{CH}_2\text{OCF}_2\text{CFOCF}_2\text{CF}_2\text{OCFCOOSi}(\text{CH}_3)_3 \quad [\text{IIId}]$$
$$\qquad\qquad\qquad\qquad\quad\ |\qquad\qquad\qquad\quad\ |$$
$$\qquad\qquad\qquad\qquad\ \ \text{CF}_3\qquad\qquad\quad\ \text{CF}_3$$

Analysis

| $^1$H-NMR: δ (ppm) | |
|---|---|
| CH$_2$= | 5.45 |
| =CH— | 6.07 |
| —CH$_2$—O— | 4.71 |
| —Si(CH$_3$)$_3$ | 0.51 |
| GC-MS | |
| (M + H)$^+$ | 557 |
| IR: | |
| >C=O | 1770 cm$^{-1}$ |

Elemental analysis:

| | C | H | O | F | Si |
|---|---|---|---|---|---|
| Calcd. (%) | 30.2 | 2.5 | 14.4 | 47.8 | 5.0 |
| Found (%) | 30.0 | 22.7 | 14.6 | 47.8 | 4.7 |

Next, a 200-ml, three-necked flask equipped with a reflux condenser, magnetic stirrer, and thermometer was charged with 80 grams of the compound of formula [IIId] prepared above. Using an oil bath, the flask was heated to keep the contents at 70° C. After 0.01 gram of a 10% toluene solution of chloroplatinic acid was added, 27.3 grams of diisopropenoxymethylsilane was slowly added through a dropping funnel. The rate of addition was controlled such that the contents were at 70° to 100° C. After the completion of addition, stirring was continued for one hour at 70° C. At the end of reaction, stirring was continued for further one hour at 70° C. Then the flask contents were poured into a distillation flask. The flask was heated by an oil bath adjusted at 80° C. while the flask interior was evacuated up to 2 mmHg by means of a vacuum pump. The volatile contents were distilled off in this way, leaving 91.0 grams of a non-volatile liquid in the flask. On analysis, this product was identified to be a compound of formula [Id] shown below. The yield was 88%.

$$\underset{\underset{CH_3}{|}}{(CH_2=\overset{\overset{CH_3}{|}}{C}-O)_2}-Si-CH_2CH_2CH_2OCF_2\underset{CF_3}{CFOCF_2}CF_2O\underset{CF_3}{CFCOOSi(CH_3)_3} \quad [Id]$$

Analysis $^1$H-NMR:

$$\underset{\underset{CH_3}{\diagup}}{\overset{\overset{CH_2}{\diagdown}}{(}}\overset{3}{C}-O)_2-\overset{}{Si}-\overset{4}{C}H_2\overset{5}{C}H_2\overset{6}{C}H_2OCF_2\underset{CF_3}{CFOCF_2}CF_2O\underset{CF_3}{CFCOO\overset{7}{Si}(CH_3)_3}$$

| | δ (ppm) |
|---|---|
| 1 | 4.21 |
| 2 | 1.97 |
| 3 | 0.34 |
| 4 | 1.02 |
| 5 | 1.92 |
| 6 | 4.18 |
| 7 | 0.51 |

GC-MS:

(M + H)⁻     715

IR:

$>$C=O     1770 cm$^{-1}$

Figure 4:
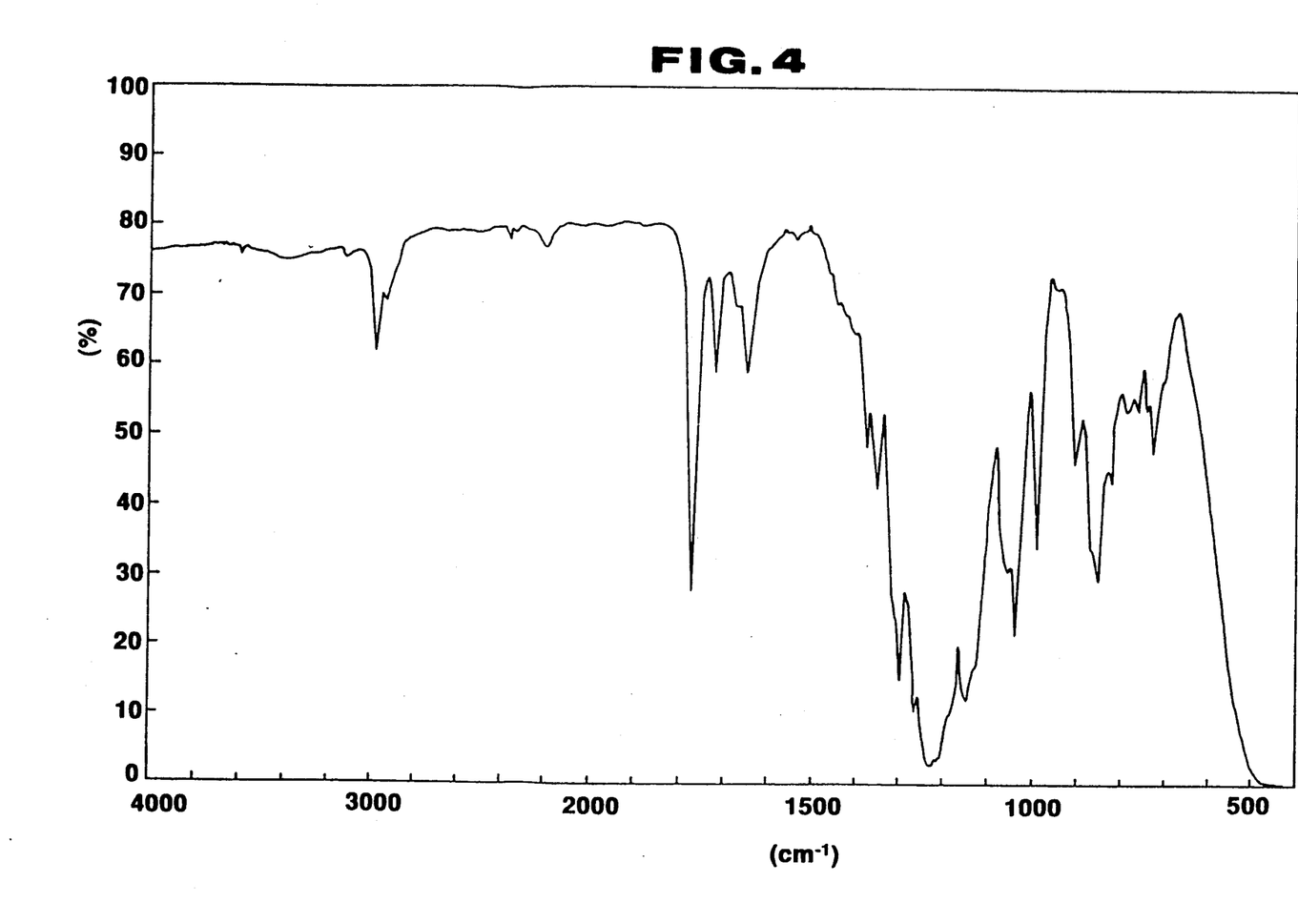

IR spectrum is shown in the chart of FIG 4.

Elemental analysis:

| | C | H | O | F | Si |
|---|---|---|---|---|---|
| Calcd. (%) | 35.3 | 3.9 | 15.7 | 37.3 | 7.8 |
| Found (%) | 35.7 | 3.6 | 15.3 | 37.8 | 7.6 |

EXAMPLE 5

A 200-ml, three-necked flask equipped with a reflux condenser, magnetic stirrer, and thermometer was charged with 80 grams of the compound of formula [IIId] obtained in Example 4. Using an oil bath, the flask was heated to keep the contents at 70° C. After 0.01 gram of a 10% toluene solution of chloroplatinic acid was added, 56.3 grams of tris(2,2,2-trifluoroethoxy)silane was slowly added through a dropping funnel. The rate of addition was controlled such that the contents were at 70° to 100° C. After the completion of addition, stirring was continued for one hour at 70° C. At the end of reaction, stirring was continued for further one hour at 70° C. Then the flask contents were poured into a distillation flask. The flask was heated by an oil bath adjusted at 80° C. while the flask interior was evacuated up to 2 mmHg by means of a vacuum pump. The volatile contents were distilled off in this way, leaving 118.2 grams of a non-volatile liquid in the flask. On analysis, this product was identified to be a compound of formula [Ie] shown below. The yield was 93%.

$$(CF_3CH_2O)_3SiCH_2CH_2CH_2OCF_2\underset{CF_3}{CFOCF_2}CF_2O\underset{CF_3}{CFCOOSi(CH_3)_3} \quad [Ie]$$

Analysis $^1$H-NMR:

$$(CF_3\overset{1}{C}H_2O)_3Si\overset{2}{C}H_2\overset{3}{C}H_2\overset{4}{C}H_2OCF_2\underset{CF_3}{CFOCF_2}CF_2O\underset{CF_3}{CFCOOSi(\overset{5}{C}H_3)_3}$$

| | δ (ppm) |
|---|---|
| 1 | 4.17 |
| 2 | 4.17 |
| 3 | 1.91 |
| 4 | 1.01 |
| 5 | 0.51 |

GC-MS:

(M + H)⁺     883

IR:

$>$C=O     1770 cm$^{-1}$

Figure 5:
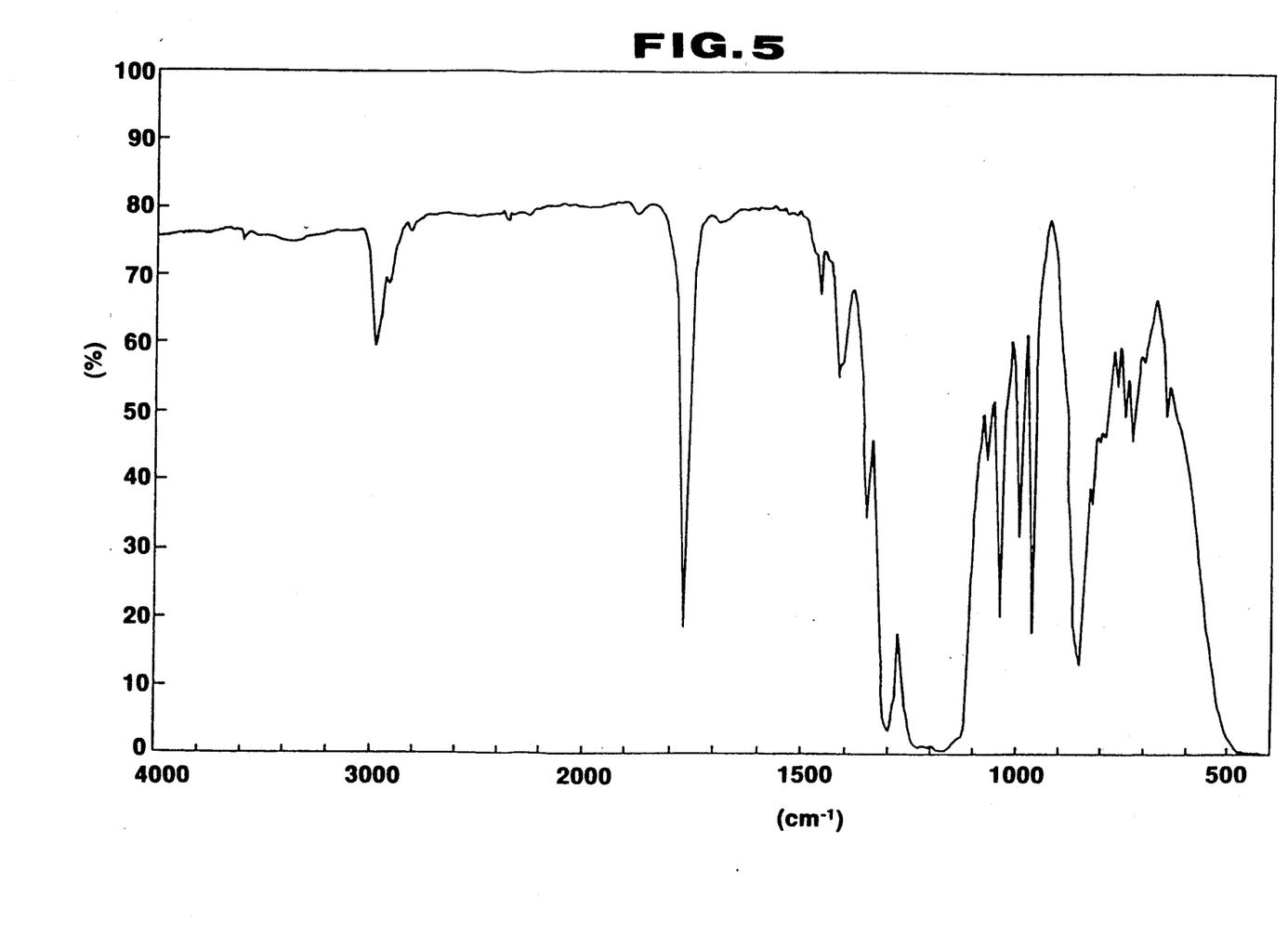

IR spectrum is shown in the chart of FIG 5.

Elemental analysis:

| | C | H | O | F | Si |
|---|---|---|---|---|---|
| Calcd. (%) | 27.2 | 2.4 | 14.5 | 49.5 | 6.4 |
| Found (%) | 27.1 | 2.3 | 14.7 | 49.3 | 6.5 |

EXAMPLE 6

A 100-ml, three-necked flask equipped with a reflux condenser, magnetic stirrer, and thermometer was charged with 50 grams of the compound of formula [Ie] obtained in Example 5. With stirring, the flask was cooled with an ice water bath until the flask contents reached 5° C. After 1.02 grams of water was added dropwise through a dropping funnel, stirring was continued for one hour while maintaining ice water cooling. Thereafter, the flask was heated by an oil bath adjusted at 50° C. while the flask interior was evacuated up to 2 mmHg by means of a vacuum pump. The volatile contents were distilled off in this way, leaving 44.7 grams of a non-volatile liquid in the flask. On analysis, this product was identified to be a compound of formula [If] shown below.

[If]

Analysis

<u>$^1$H-NMR:</u>

| | δ (ppm) |
|---|---|
| 1 | 4.17 |
| 2 | 4.17 |
| 3 | 1.91 |
| 4 | 1.01 |
| 5 | 11.5 |

<u>GC-MS:</u>

(M + H)$^+$  811

<u>IR:</u>

1780 cm$^{-1}$

—OH  3200 cm$^{-1}$

Figure 6:
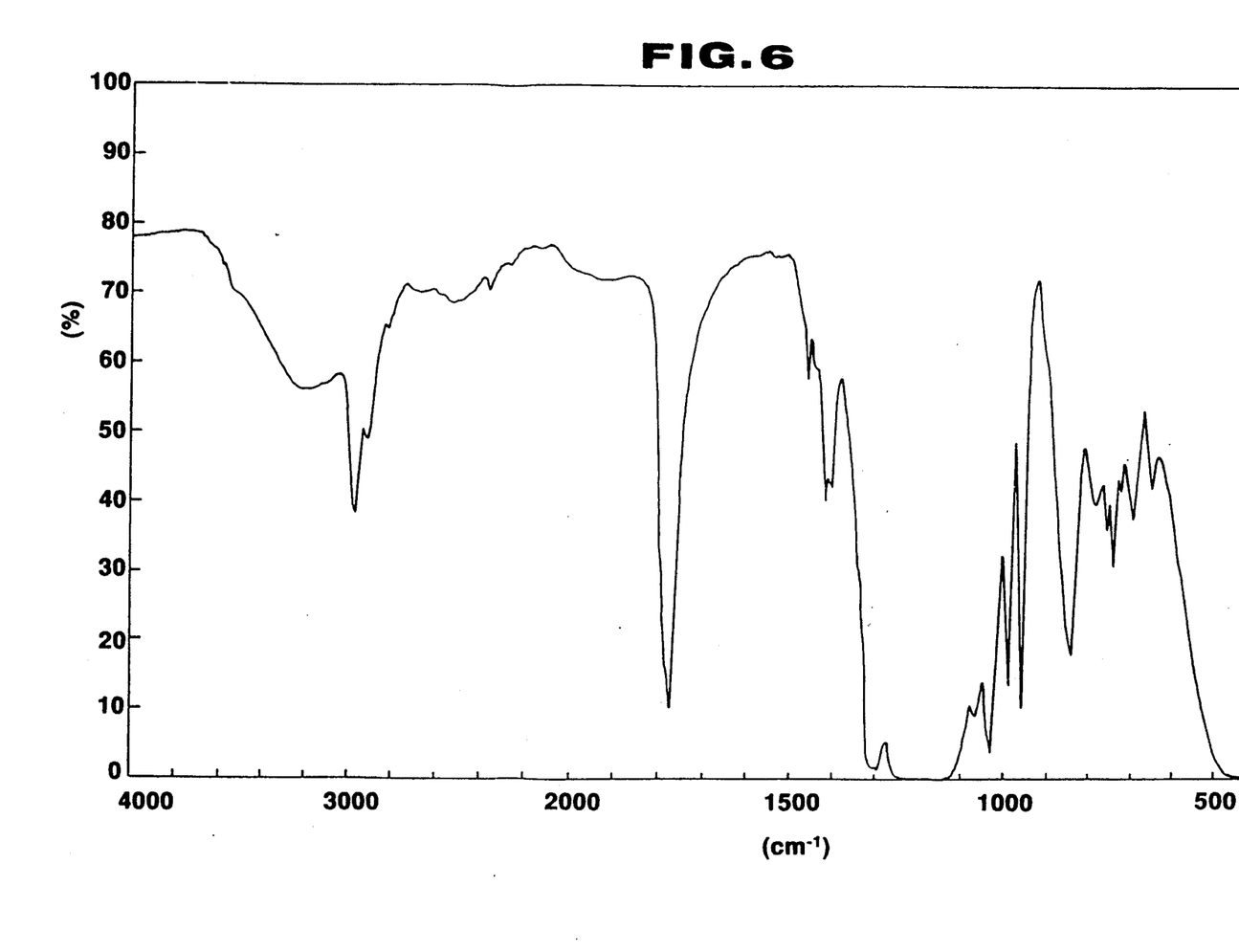

IR spectrum is shown in the chart of FIG. 6.

Elemental analysis:

| | C | H | O | F | Si |
|---|---|---|---|---|---|
| Calcd. (%) | 25.2 | 1.6 | 15.8 | 54.0 | 3.4 |
| Found (%) | 24.8 | 1.7 | 15.3 | 54.5 | 3.6 |

REFERENCE EXAMPLE 1

Composition I was prepared by blending 100 parts of a dimethylpolysiloxane blocked with a hydroxyl group at each end of its molecular chain having a viscosity of 20,200 centipoise at 25° C., 12 parts of fumed silica surface treated with hexamethyldisilazane having a specific surface area of 150 m$^2$/g, and 1.5 parts of titanium dioxide, and passing the blend through a three-roll mill once. The blend was further mixed with 6 parts of methyltriisopropenoxysilane and 0.5 parts of the perfluorocarboxylic derivative of the formula:

obtained in Example 5 in an anhydrous condition while defoaming.

Composition I was formed into a sheet of 2 mm thick and allowed to stand for 7 days in an atmosphere at a temperature of 20° C. and a relative humidity of 55%. This caused the sheet to cure into a rubbery elastomer Ia.

Composition I remained stable over 6 months at room temperature if sealed against the ambient. This 6-month aged composition I was also formed into a sheet of 2 mm thick which was cured under the same conditions as above into a rubbery elastomer Ib. The elastomers obtained from the fresh and aged compositions were examined for physical properties (hardness, tensile strength and elongation) according to JIS C-2123.

Further, rubbery elastomer Ia was exposed to 200° C. for 7 days for thermal degradation. This thermally degraded rubbery elastomer Ic was similarly examined for physical properties.

The results are shown in Table 1.

TABLE 1

| | Initial Elastomer Ia | Aged @ 20° C./6 month Elastomer Ib | Heated @ 200° C./7 days Elastomer Ic |
|---|---|---|---|
| Hardness, JIS-A | 29 | 31 | 33 |
| Tensile strength, kg/cm$^2$ | 20 | 19 | 21 |
| Elongation, % | 350 | 330 | 270 |

In addition, Composition I was tested by the metal corrosion test as prescribed in MIL-A-46146A.

TEST METHOD 1

Composition I, 15 grams, was placed in a 250-ml container. Onto Composition I was poured 5 to 10 ml of distilled water. A clean test piece was suspended above the water surface. The container was sealed at the top. The container was allowed to stand for 168 hours at 38° C. The test piece was visually observed for corrosion.

TEST METHOD 2

A test piece was cleaned with acetone and coated with Composition I, which was cured for 7 days at 25° C. and RH 50%. The test piece was then allowed to stand for 28 days at 49° C. and RH 98%. The rubbery elastomer coating was stripped using a knife. The surface of the test piece from which the coating and stripped was visually observed for corrosion.

The results are shown in Table 2.

TABLE 2

| | Test piece | Result |
|---|---|---|
| Test method 1 | Brass | no corrosion |
| | Steel | no corrosion |
| | Aluminum | no corrosion |
| Test method 2 | Copper wire | no corrosion |
| | Steel | no corrosion |
| | Aluminum | no corrosion |

Rubbery elastomer Ia resulting from curing of Composition I was measured for a change of color at the initial, after heating at 90° C. for 168 hours, and after weatherometer exposure for 168 hours, using a differential colorimeter.

For comparison purposes, Composition II was prepared which had the same formulation as Composition I except that 0.5 parts of a guanidine derivative of the formula:

was used instead of the perfluorocarboxylic derivative. A cured sheet of 2 mm thick was formed from Composition II by the same procedure as described for Composition I and subjected to a discoloration test.

The results are shown in Table 3.

TABLE 3

| | Composition I | | | | Composition II | | | |
|---|---|---|---|---|---|---|---|---|
| | L | a | b | ΔE | L | a | b | ΔE |
| Initial | 94.2 | −0.3 | 1.9 | — | 92.6 | −0.9 | 2.5 | — |
| 90° C./168 hr. | 93.6 | −1.8 | 7.7 | 6.0 | 88.2 | −3.6 | 18.2 | 16.5 |

TABLE 3-continued

|  | Composition I | | | | Composition II | | | |
| --- | --- | --- | --- | --- | --- | --- | --- | --- |
|  | L | a | b | ΔE | L | a | b | ΔE |
| Weathering | 94.0 | −0.7 | 3.6 | 1.7 | 90.6 | −2.8 | 12.2 | 10.1 |

Discoloration $\Delta E = [(\Delta L)^2 + (\Delta a)^2 + (\Delta b)^2]^{\frac{1}{2}}$

REFERENCE EXAMPLE 2

Composition III was prepared by blending 100 parts of 3,3,3-trifluoropropylmethylpolysiloxane blocked with a hydroxyl group at each end of its molecular chain having a viscosity of 62,300 centipoise at 25° C. and 8 parts of fumed silica surface treated with dimethyldichlorosilane having a specific surface area of 180 m²/g and passing the blend through a three-roll mill once. The blend was further mixed with 6 parts of vinyltriisopropenoxysilane, 0.4 parts of the perfluorocarboxylic derivative of the formula:

$$(CF_3CH_2O)_3SiCH_2CH_2CH_2OCF_2CFOCF_2CF_2OCFCOOSi(CH_3)_3$$
$$\qquad\qquad\qquad\qquad\qquad\quad |\qquad\qquad\quad |$$
$$\qquad\qquad\qquad\qquad\qquad\;\; CF_3\qquad\qquad CF_3$$

obtained in Example 5, and 0.1 part of dibutyltindioctoate in an anhydrous condition while defoaming.

Composition III was formed into a sheet of 2 mm thick and allowed to stand for 7 days in an atmosphere at a temperature of 20° C. and a relative humidity of 55%. This caused the sheet to cure into a rubbery elastomer IIIa.

Composition III remained stable over 6 months at room temperature if sealed against the ambient. This 6-month aged composition III was also formed into a sheet of 2 mm thick which was cured under the same conditions as above into a rubbery elastomer IIIb. The elastomers obtained from the fresh and aged compositions were examined for physical properties (hardness, tensile strength and elongation) according to JIS C-2123.

Further, rubbery elastomer IIIa was exposed to 200° C. for 7 days for thermal degradation. This thermally degraded rubbery elastomer IIIc was similarly examined for physical properties.

The results are shown in Table 4.

TABLE 4

| Elastomer | Initial IIIa | Aged @ 20° C./6 month IIIb | Heated @ 200° C./7 days IIIc |
| --- | --- | --- | --- |
| Hardness, JIS-A | 27 | 28 | 33 |
| Tensile strength, kg/cm² | 25 | 23 | 17 |
| Elongation, % | 280 | 260 | 200 |

In addition, Composition III was tested for metal corrosion as previously described. The results are shown in Table 5.

TABLE 5

|  | Test piece | Result |
| --- | --- | --- |
| Test method 1 | Brass | no corrosion |
|  | Steel | no corrosion |
|  | Aluminum | no corrosion |
| Test method 2 | Copper wire | no corrosion |
|  | Steel | no corrosion |
|  | Aluminum | no corrosion |

REFERENCE EXAMPLE 3

Composition IV was prepared by blending 100 parts of a dimethylpolysiloxane blocked with a hydroxyl group at each end of its molecular chain having a viscosity of 10,500 centipoise at 25° C. and 10 parts of carbon powder and passing the blend through a three-roll mill once. The blend was further mixed with 7 parts of phenyltriisopropenoxysilane and 0.4 parts of the perfluorocarboxylic derivative of the formula:

$$(CH_3O)_3SiCH_2CH_2CH_2O(CF_2)_5COOSi(CH_3)_3$$

obtained in Example 1 in an anhydrous condition while defoaming.

Composition IV was formed into a sheet of 2 mm thick and allowed to stand for 7 days in an atmosphere at a temperature of 20° C. and a relative humidity of 55%. This caused the sheet to cure into a rubbery elastomer IVa.

Composition IV remained stable over 6 months at room temperature if sealed against the ambient. This 6-month aged composition IV was also formed into a sheet of 2 mm thick which was cured under the same conditions as above into a rubbery elastomer IVb. The elastomers obtained from the fresh and aged compositions were examined for physical properties (hardness, tensile strength and elongation) according to JIS C-2123.

The results are shown in Table 6.

TABLE 6

|  | Initial Elastomer IVa | Aged @ 20° C./6 month Elastomer IVb |
| --- | --- | --- |
| Hardness, JIS-A | 25 | 26 |
| Tensile strength, kg/cm² | 17 | 18 |
| Elongation, % | 250 | 230 |

Although some preferred embodiments have been described, many modifications and variations may be made thereto in the light of the above teachings. It is therefore to be understood that within the scope of the appended claims, the invention may be practiced otherwise than as specifically described.

We claim:

1. A fluorinated carboxylic acid derivative of the general formula:

$$(R^1O)_a - \underset{\underset{R^2_{3-a}}{|}}{Si} - (CH_2)_3 - O - CF_2 - Rf - \overset{\overset{O}{\|}}{C} - OX \qquad [I]$$

wherein $R^1$ and $R^2$ are independently selected from substituted or unsubstituted monovalent hydrocarbon groups, Rf is a divalent perfluoroalkyl or perfluoropolyether group of the general formula:

$$-(CFO)_j - (CF_2CFO)_m - (CF_2)_n - (OCFCF_2)_l - (OCF)_k -$$
$$\quad\; |\qquad\qquad |\qquad\qquad\qquad\qquad |\qquad\qquad |$$
$$\;\; CF_3\qquad\;\; CF_3\qquad\qquad\qquad CF_3\qquad\; CF_3$$

wherein n is an integer of from 0 to 8, m and l are integers of from 0 to 3, j and k are each equal to 0 or 1, with the proviso that j=k=l=m=0 when n=0, m=0 when j=0, and l=0 when k=0, X is a hydrogen atom or triorganosilyl group, and letter a is equal to 2 or 3.

2. The fluorinated carboxylic acid derivative according to claim 1, wherein $R^1$ of general formula is an alkyl group, an alkenyl group, a cycloalkyl group, an aryl group, an alkenyloxy group or a haloalkyl group.

3. The fluorinated carboxylic acid derivative according to claim 1, wherein $R^2$ of general formula is an alkyl group, an alkenyl group, a cycloalkyl group, an aryl group or a haloalkyl group.

4. The fluorinated carboxylic acid derivative according to claim 1, wherein $R^1$ of general formula is methyl, ethyl, propyl, vinyl, allyl, cyclopentyl, cyclohexyl, phenyl, tolyl, isopropenoxy, isobutenoxy, 2,2,2-trifluoroethoxy or 3,3,3-trifluoro-2-trifluoropropoxy.

5. The fluorinated carboxylic acid derivative according to claim 1, wherein $R^2$ of general formula is methyl, ethyl, propyl, vinyl, allyl, cyclopentyl, cyclohexyl, phenyl, tolyl, 3,3,3-trifluoropropyl or 3,3,4,4,5,5,6,6,6-nonafluorohexyl.

6. A fluorinated carboxylic acid derivative of the formula:

$(CH_3O)_3Si(CH_2)_3OCF_2COOH$,

$(F_3CCH_2O)_3Si(CH_2O)_3OCF_2COOSi(CH_3)_3$, $(CH_3O)_3Si(CH_2)_3O(CF_2)_4COOH$, $(CH_3O)_3Si(CH_2)_3O(CF_2)_5COOSi(CH_3)_3$, $(CF_3CH_2O)_3Si(CH_2)_3O(CF_2)_5COOSi(CH_3)_3$, $(CF_3CH_2O)_3Si(CH_2)_3O(CF_2)_5COOSi(CH_3)_2$
              |
              $CH=CH_2$ $(CF_3CH_2O)_3Si(CH_2)_3O(CF_2)_5COOSi(CH_3)_2$, $(CF_3CH_2O)_2Si(CH_2)_3O(CF_2)_5COOH$,
         |
        $CH_3$ $(CH_2=CO)_2Si(CH_2)_3O(CF_2)_5COOSi(CH_3)_3$,
       |       |
      $CH_3$  $CH_3$ $(CF_3CH_2O)_3Si(CH_2)_3OCF_2CFOCF_2CF_2OCFCOOSi(CH_3)_3$,
                        |                |
                       $CF_3$           $CF_3$ $(CF_3CH_2O)_2Si(CH_2)_3OCF_2CFOCF_2CF_2OCFCOOSi(CH_3)_3$,
         |              |                |
        $CH_3$         $CF_3$           $CF_3$ $(CF_3CH_2O)_3Si(CH_2)_3OCF_2CFOCF_2CF_2OCFCOOH$ or
                        |                |
                       $CF_3$           $CF_3$ $(CH_2=CO)_2Si(CH_2)_3OCF_2CFOCF_2CF_2OCFCOOSi(CH_3)_3$.
       |       |        |                |
      $CH_3$  $CH_3$   $CF_3$           $CF_3$

* * * * *